US010048244B2

(12) United States Patent
Rodgers et al.

(10) Patent No.: US 10,048,244 B2
(45) Date of Patent: Aug. 14, 2018

(54) DETERMINATION OF THE DISTRIBUTION OF REACTIVE AND NON-REACTIVE SULFUR IN PETROLEUM AND ITS FRACTIONS

(71) Applicant: FLORIDA STATE UNIVERSITY RESEARCH FOUNDATION, INC., Tallahassee, FL (US)

(72) Inventors: Ryan P. Rodgers, Tallahassee, FL (US); Winston K. Robbins, Brunswick, ME (US); Vladislav V. Lobodin, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 0 days.

(21) Appl. No.: 14/776,077

(22) PCT Filed: Mar. 13, 2014

(86) PCT No.: PCT/US2014/025784
§ 371 (c)(1),
(2) Date: Sep. 14, 2015

(87) PCT Pub. No.: WO2014/151460
PCT Pub. Date: Sep. 25, 2014

(65) Prior Publication Data
US 2016/0025699 A1    Jan. 28, 2016

Related U.S. Application Data

(60) Provisional application No. 61/864,406, filed on Aug. 9, 2013, provisional application No. 61/794,291, filed on Mar. 15, 2013.

(51) Int. Cl.
*G01N 33/00* (2006.01)
*G01N 33/28* (2006.01)
(Continued)

(52) U.S. Cl.
CPC ....... *G01N 33/287* (2013.01); *B01D 15/3828* (2013.01); *B01J 45/00* (2013.01);
(Continued)

(58) Field of Classification Search
CPC .................................................. G01N 33/287
(Continued)

(56) References Cited

U.S. PATENT DOCUMENTS 4,354,928 A * 10/1982 Audeh ............... B01D 11/0203
208/309
4,430,205 A * 2/1984 Felsky ................... C10G 25/00
208/14
(Continued)

OTHER PUBLICATIONS

Abstract: Michael L. Hair "Hydroxyl groups on silica surface" Journal of Non-Crystalline Solids vol. 19, Dec. 1975, pp. 299-309.*
(Continued)

*Primary Examiner* — Christopher Adam Hixson
*Assistant Examiner* — Emily R. Berkeley
(74) *Attorney, Agent, or Firm* — Fox Rothschild LLP (57) ABSTRACT

A method to determine the distribution of non-reactive sulfur compounds and reactive sulfur compounds in petroleum samples by separating non-reactive sulfur compounds from reactive sulfur compounds in a petroleum composition includes the step of contacting the petroleum composition with a Ag-containing cation exchange media. The petroleum composition and the Ag-containing cation exchange media are contacted with a non-reactive sulfur compound solvent capable of eluting the non-reactive sulfur compounds in the presence of the Ag-containing cation exchange media and incapable of eluting the reactive sulfur compounds in the presence of the Ag-containing cation exchange media at the conditions of the exchange. The non-reactive sulfur compounds are eluted from the media with the non-reactive sulfur compound solvent to provide a first fraction. The amount of non-reactive sulfur compounds in the first fraction is then determined.

11 Claims, 10 Drawing Sheets

(51) Int. Cl.
- *B01D 15/38* (2006.01)
- *B01J 45/00* (2006.01)
- *B01D 15/36* (2006.01)
- *G01N 30/96* (2006.01)
- *G01N 30/88* (2006.01)

(52) U.S. Cl.
CPC ............ *B01D 15/362* (2013.01); *G01N 30/96* (2013.01); *G01N 2030/8854* (2013.01)

(58) Field of Classification Search
USPC .......................................................... 436/91
See application file for complete search history.

(56) References Cited

U.S. PATENT DOCUMENTS

| | | | | |
|---|---|---|---|---|
| 5,744,702 A | * | 4/1998 | Roussis | G01N 33/287 73/53.01 |
| 2010/0218585 A1 | * | 9/2010 | Chawla | G01N 30/462 73/1.02 |

OTHER PUBLICATIONS

Adsorption (https://web.archive.org/web/20120117052529/http://www.chem.qmul.ac.uk/surfaces/scc/scat2_2.htm) Captured Jan. 17, 2012.*

AOCS (http://lipidlibrary.aocs.org/Analysis/content.cfm?ItemNumber=40348) Mar. 29, 2011.*

International Search Report from PCT/US2014/025784 dated Jul. 11, 2014.

Diversified Enterprises. Surface Tension, Hansen Solubility Parameters, Molar Volume, Enthalpy of Evaporation, and Molecular Weight of Selected Liquids. [Retrieved on Jun. 13, 2014]. Retrieved from the internet. <URL: http://www.accudynetest.com/solubility_table.html>.

Safe Processing of Acid Crudes, Corrosion 2004, Paper No. 04637. Sergio D. Kapusta et al., pp. 1-19.

Andersson et al.: "Polycyclic Aromatic Sulfur Heterocycles in Desulfurized Diesel Fuels and Their Separation on a Novel Palladium(II)-Complex Stationary Phase", Polycyclic Aromatic Compounds, 22:311-320, 2002.

"Retention Properties of a Palladium Chloride/Silica Sorbent for the Liquid Chromatographic Separation of Polycyclic Aromatic Sulfur Heterocycles" Anal. Chem. 1987, 59, 2207-2209.

Wang et al.: "Approach for Selective Separation of Thiophenic and Sutfidic Sulfur Compounds from Petroleum by Methylation/Demethylation" Anal. Chem., 2015, 87 (2), pp. 1083-1088.

Japes et al.: "Analysis of Recalcitrant Hexahydrodibenzothiophenes in Petroleum Products Using a Simple Fractionation Process" Energy Fuels, 2009, 23 (4), pp. 2143-2148.

Payzant et al.: "Improved Methods for the Selective Isolation of the Sulfide and Thiophenic Classes of Compounds from Petroleum" Energy & Fuels 1989,3, 449-454.

* cited by examiner

DETERMINATION OF THE DISTRIBUTION OF REACTIVE AND NON-REACTIVE SULFUR IN PETROLEUM AND ITS FRACTIONS

CROSS REFERENCE TO RELATED APPLICATIONS

This application is a § 371 National Stage application of International Patent Application No. PCT/US14/25784, filed Mar. 13, 2014 and entitled "DETERMINATION OF THE DISTRIBUTION OF REACTIVE AND NON-REACTIVE SULFU IN PETROLEUM AND ITS FRACTIONS", which claims the priority of U.S. Provisional Patent Applications 61/794,291 filed Mar. 15, 2013 and 61/864,406 filed Aug. 9, 2013. The disclosures of which are hereby fully incorporated by reference.

STATEMENT REGARDING FEDERALLY SPONSORED RESEARCH

This invention was made with government support under contract No. DMR-06-54118 awarded by the National Science Foundation. The government has certain rights in this invention. The invention was also funded by the Future Fuels Institute.

FIELD OF THE INVENTION

The present invention relates to petroleum testing methodology, and more specifically to methodology for testing for the content of sulfur compounds in petroleum compositions.

BACKGROUND OF THE INVENTION

Sulfur compounds in petroleum present an enormous variety of chemical structures and are described by chemical classes (thiols, disulfides, sulfides, thiophenes, etc.). The relative stability of various sulfur species are considerably different; sulfides, disulfides and thiols in the petroleum feed stocks are more easily desulfurized during desulfurization processes on a refinery than the aromatic sulfur compounds. Compounds containing sulfur atom in an aliphatic structure (e.g. thiols, sulfides, disulfides) are more reactive (hence more corrosive) than compounds with the sulfur atom in an aromatic ring structure (e.g. thiophenes, benzothiophenes, dibenzothiophenes, etc.). Therefore, the sulfur compounds in the product stream of a desulfurization process are mostly in aromatic form and are considered more unsusceptible (non-reactive sulfur) to desulfurization processes. Among these, the substituted benzothiophenes and dibenzothiophenes are the most difficult to remove compared to unsubstituted thiophenes, benzothiophenes, or dibenzothiophenes. It is also well recognized by industry that each of these classes contributes differently to corrosion at high temperatures in a refinery. Thus, determination of the corrosive behavior of oils requires an assessment of sulfur containing organic compounds that it contains. The term "reactive sulfur" can be defined as the organic sulfur that generates $H_2S$ under thermal stress or relatively easy to remove by desulfurization. Research indicates that such compounds (non-aromatic mercaptans, sulfides, and disulfides) are corrosive in refinery stress at temperatures between 250-400° C. (450-700° F.). Thermally stable organosulfur compounds (thiophenes, thiophenols, and aryl sulfides where sulfur electrons are conjugated with the aromatic ring) are termed "non-reactive". It will be recognized by those familiar with refinery operations that the "corrosive" sulfur classes are also the most reactive in common refinery processes such as hydrotreating, cracking or coking while the "non-corrosive" thiophenic are the least "reactive". Thus, the instant invention applies equally to the distinction of reactivity. This application will use the terms "reactive" and "non-reactive" with the understanding that the alternative corrosiveness designation applies equally well.

Thiophenes are generally considered to be the dominant form of organic S in petroleum fractions boiling in the critical temperature range; consequently, total sulfur analyses do not reflect the concentration of reactive sulfur. Indigenous $H_2S$ and elemental S are measured by existing routine techniques, if necessary.

Cataldi (1953) proposed to measure "corrosive potential" by determination of $H_2S$ evolution at 800° C. Alternatively, Drushel (1956) proposed measuring total S before and after high temperature pyrolysis over a catalytic surface to determine the "thiophenic" and "non-thiophenic" sulfur. Piehl (1960) expanded on this concept by measuring the $H_2S$ evolution while heating crudes in glass at 2° F./min. Other research has suggested that chemisorption of corrosive sulfur compounds onto metal surfaces initiates $H_2S$ evolution at lower temperature.

As an alternative to $H_2S$ evolution, it has been proposed that oils be characterized by a combination of different analytical techniques. In 1974, an API study group reported a scheme wherein oils have been characterized by suite of analytical procedures for the determination of all classes of S (S, $H_2S$, mercaptans, sulfides, disulfides, and thiophenes by difference). Various refinements of these techniques have evolved for the measurement of specific classes especially for the measurement of sulfides. In particular, techniques have been developed based on iodine complexes and UV measurement, oxidation coupled FTIR measurement, oxidative titration to end points, XPS and XANES. These techniques characterize and quantify S in molecular species based on "average" molecular structures rather than measuring the S content directly. In addition multi-step oxidation/reduction procedures have been combined with chromatography for the isolation of sulfur molecular species which are then characterized by sophisticated techniques such as GC/MS or FT-ICR MS. The latter technique qualitatively characterizes the molecular character after conversion of sulfides to ionizable derivatives (sulfoxides or methylsulfonium salts). A number of techniques which involve the formation of complexes with various sulfur compound classes with metal cations (Hg, Ag, Cu, and Pd) have been utilized for the separation of sulfur compounds. Historically, concentrated solutions of mercury salts were used to precipitate thiols (hence the name mercaptans) and a few lower MW sulfides from low boiling distillates. More recently, Ag(I) and Pd(II) impregnated adsorbents were used to resolve thiophenics from aromatic compounds. On 5% $PdCl_2$ impregnated silica, aromatics are eluted with a moderate polarity solvent mixture (hexane chloroform) while with thiophenics were retained until eluted as Pd-salts with a chloroform:ether mixture. Because ether contains 2% ethanol as stabilizer, alcohol-soluble thiophene-Pd complexes were removed. Sulfide-Pd complexes are only recovered with the use of much higher concentrations of alcohol. (Both S species were "sprung" from Pd with amines.) Cation exchange resins converted to their $Ag^+$ form have been used to separate thiophenes from aromatic hydrocarbons. In some cases, sulfides are recovered by ligand exchange displacement by excess dimethylsulfide. More recently, Ag(I) forms of cation exchangers bound to silica have been used for the same purpose. While much of the emphasis has been on the use of Pd(II) for the separation of thiophenics from aromatics, Cu(II) and Ag(I) have been used for the separation of sulfides as well. In one example of the latter, the silver forms of a strong cation exchange (SCX) silica has been incorporated into a complex HPLC separation that isolates a "sulfide" fraction from saturates, four ring sizes of aromatics and polars. In this instance, the sulfides are recovered by back-flush with an alcohol rich solvent but the distribution of sulfur is not determined.

SUMMARY OF THE INVENTION

A method to determine the distribution of non-reactive sulfur compounds and reactive sulfur compounds in petroleum samples by separating non-reactive sulfur compounds from reactive sulfur compounds in a petroleum composition includes the step of contacting the petroleum composition with a Ag-containing cation exchange media. The petroleum composition and the Ag-containing cation exchange media are contacted with a non-reactive sulfur compound solvent capable of eluting the non-reactive sulfur compounds in the presence of the Ag-containing cation exchange media and incapable of eluting the reactive sulfur compounds in the presence of the Ag-containing cation exchange media at the conditions of the exchange. The non-reactive sulfur compounds are eluted from the media with the non-reactive sulfur compound solvent to provide a first fraction. The amount of non-reactive sulfur compounds in the first fraction is then determined.

The method can further comprise the step of, after the step of eluting the non-reactive sulfur compounds, eluting the reactive sulfur compounds with a reactive sulfur compound solvent to provide a second fraction. The reactive sulfur compound solvent is capable of eluting the reactive sulfur compounds in the presence of the Ag-containing cation exchange media. The amount of reactive sulfur compounds in the second fraction can be determined.

The media can be at least one selected from the group consisting of silica, polymer, or nano-dispersed media.

The reactive sulfur compounds can comprise at least one selected from the group consisting of mercaptans, disulfides, and sulfides. The reactive sulfur compounds comprise at least one selected from the group consisting of:

$R_1$SH—Thiol (mercaptans)

$R_1SR_2$—Sulfides (including cyclic)

$R_1SSR_2$—Disulfides where $R_1$, $R_2$ can be H, alkyl, cycloalky or aryl groups connecting to S-atom directly or through alkyl groups, and $R_1$, $R_2$ can further comprise heteroatoms (O,N,S). Diaryl sulfides are considered to be non-reactive sulfur compounds.

The non-corrosive sulfur compounds can comprise thiophenic sulfur compounds and diaryl sulfides. The non-corrosive sulfur compounds comprise at least one selected from the group consisting of:

-continued

The non-reactive sulfur compound solvent can have Hansen solubility parameters of $\delta_d$=17-20; $\delta_p$=0-7.0; and $\delta_h$<7. The non-reactive sulfur compound solvent can be at least one selected from the group consisting of toluene, dichloromethane, and acetone.

The method can include the step of eluting the reactive sulfur compounds with a reactive sulfur compound solvent (Hansen solubility parameters: $\delta_d$=15-20; $\delta_p$>7; and $\delta_h$>6).

The method can include the step of measuring the sulfur content of the eluted non-reactive sulfur compounds. The method can include the step of eluting the reactive sulfur compounds with a reactive sulfur compound solvent, and measuring the sulfur content of the eluted reactive sulfur compounds. The method can also include the step of calculating the sulfur content from mercaptans in the reactive sulfur compounds.

The method can include the step of determining the total sulfur content of the petroleum sample, and determining the sulfur content of the reactive sulfur compounds from the total sulfur content and the sulfur content of the non-reactive sulfur compounds. The method can include the step of diluting the petroleum composition with an organic solvent prior to contacting the petroleum composition with the Ag-containing cation exchange media. The non-reactive sulfur compound solvent can be a supercritical fluid at the conditions of the exchange.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

The distribution of reactive and non-reactive sulfur in petroleum and its fractions is accomplished by the separation of the relevant classes of sulfur compounds by ligand exchange chromatography combined with determination of sulfur content in the initial oil and its separated fractions by appropriate analytical measurements.

The distribution of sulfur into reactive and non-reactive types in crude oils and its distillate fractions allows improved planning for corrosion control in crude distillation units and optimization conditions/facilities for hydrodesulfurization. In the future, the separated fractions may be characterized by sophisticated analytical techniques for enhanced prediction of reactivity and corrosiveness.

In the instant invention, a cation exchange sorbent (either a silica or polymer-based phase) in a column or cartridge is converted to its Ag form and conditioned before a sample is eluted into two fractions. One solvent mixture elutes non-reactive sulfur compounds (thiophenics and aryl sulfides) into the first fraction. A second solvent mixture, including at least one component that forms ligands with $Ag^+$, elutes reactive S-compounds (nonaromatic sulfides and disulfides) in the second fraction. Mercaptans (thiols) irreversibly react with the silver-ion to form silver thiolates that are insoluble in the solvent mixtures employed. While the silver thiolates remain on the column, they may be recovered through additional treatment under severe conditions. By analyzing the initial sample and the two fractions by appropriate sulfur measurement techniques, it is possible to calculate the distribution of total S into non-reactive (thiophenic) and two reactive types. The latter consists of reactive sulfide/disulfides that elute in the second fraction and the mercaptans (difference between the initial S and sum of the fractions). Thus, the invention provides a convenient methodology for quantifying the distribution of reactive and non-reactive S-types in petroleum and its distillate fractions. Note that while the primary objective of this method is to separate the sulfur into fractions relating to reactivity, it will be recognized by those skilled in the art that the "corrosive" S-types are also the more reactive in most refinery processes (i.e. hydrotreating, cracking and coking) than are the "non-corrosive" thiophenic and aromatic sulfides (where the S bonding is incorporated into the aromatic $\pi$-$\pi$ bonding). Thus, the separation could be described equally as well as a method for the separation of "corrosive" and "non-corrosive" sulfur types.

The ligand exchange chromatography (LEC) separation takes advantage of the different sulfur compound type bonding with the d-orbitals of the Ag. Unlike other "LEC" applications that rely on back flushing with a polar protic solvent like methanol, the sulfides are recovered in instant invention with solvents that also form ligand complexes with $Ag^+$, for example, acetonitrile. As in other LEC with Ag-SCX applications thiophenic sulfur compounds are eluted with solvents of weak polarity (such as toluene or methylene chloride) while sulfides are recovered by ligand exchange with a reasonable volume of complexing solvent without backflush.

The fractions generated by this column or cartridge separation are also suited for subsequent characterization of the isolated fractions by sophisticated methods such as those described above. A sequence of solvent mixtures with similar characteristics can be incorporated into a HPLC separation without any need for back-flushing.

Alternate solvent combinations and sorbents can be considered to broaden the scope of the invention. Several options are being pursued to determine the most appropriate method for sulfur analysis. The separation with the solvent systems described has been validated with model compounds by GC/MS analysis of isolated fractions for a number of crude oils and distillate fractions. Once other analytical technique(s) for quantifying sulfur have been optimized, additional samples can be analyzed to generate a wider database.

A Ag-SCX silica has been incorporated into a complex HPLC separation that isolates a "sulfide" fraction from saturates, four aromatic ring types (benzenes, naphthalenes, phenanthrenes, etc) and polars. In this instance, the sulfides are recovered by back-flush with an alcohol-rich solvent and mass of organosulfur compounds (non-reactive sulfur) is determined. In some instances, the organosulfur compounds are characterized by high resolution MS following that separation.

The instant invention has value in that it can improve prediction and control of corrosive sulfur in petroleum refining. The measurement of "corrosive" sulfur in various refinery fractions represents a significant improvement over current practice that relies on total % S. Because the fractions isolated by the instant invention are also available, they can be evaluated by more sophisticated techniques that provide molecular speciation. In addition, the invention may also contribute to the understanding of the formation of crude oil (upstream geochemistry), to influence oil field development, and to follow the effects of refinery processes on sulfur classes for refinery streams from different crudes.

As noted, reactive sulfur includes mercaptans, disulfides, and sulfides. A generic representation of sulfur types has been published which shows that the fraction of thiophenic, i.e. non-reactive sulfur increases with petroleum cut point. Although there are "rules of thumb" about the proportion of thiophenic sulfur, in reality the proportion varies widely with crude source. Processing changes this distribution and the most common source for characterizing sulfur types in processed streams is experience. A method for determining levels of reactive sulfur in refinery streams can aid in the safe process optimization. It might be noted that the same reactive sulfur species involved in corrosion also contribute to heat exchanger fouling, catalyst poisoning, and $H_2S$ evolution. Conversely, the thiophenic species require more severe processing conditions. Thus, it is particularly useful to segregate the "corrosive" (i.e. reactive) and "non-corrosive" (i.e. non-reactive) types of sulfur compounds for refinery optimization.

Figure 1:
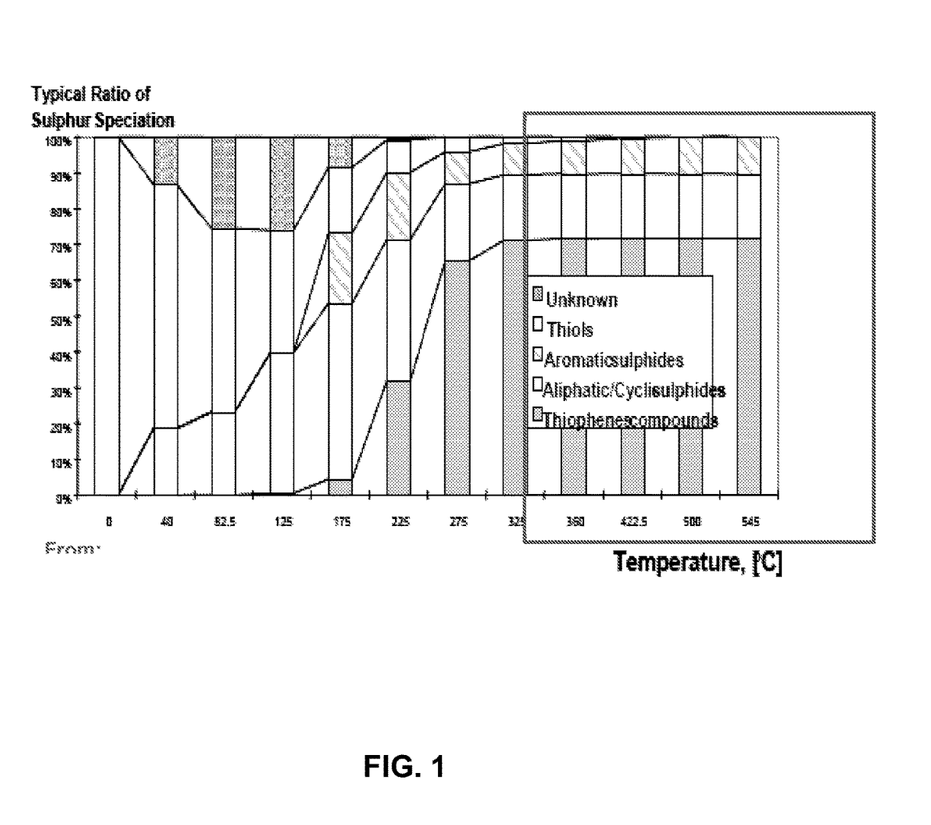
FIG. 1 is an example of sulfur speciation in a petroleum sample.

Different classes of sulfur compounds that are present (see FIG. 1, for example, from Kapusta Corrosion 2004) are separated on the Ag-SCX media on the basis of their ability to form ligand complexes with the Ag+ ionically bound to the surface sulfonic acid groups. In non-corrosive thiophenic compounds, some sulfur electrons are incorporated into the aromatic bonding weakening its ability to complex with the Ag+. On the other hand, reactive sulfur compounds, especially sulfides complex well with the electron deficient Ag+ ion on the substrate surface. Mercaptans represent a special subset of corrosive sulfur. These compounds react with the Ag+ irreversibly and are not eluted from the substrate under the conditions used.

The instant invention is based on the ability of the Ag-SCX to retain the reactive sulfur. Thiophenic compounds are eluted from the column with non-complexing solvents of moderate solvent strength, as defined by Hansen solubility parameters $(\delta_d, \delta_p, \delta_h, (MPa)^{1/2})$: $\delta_d$=17-20; $\delta_p$=0-7.0; and $\delta_h$<7. Examples of suitable solvents include, but are not restricted to mixtures of toluene, dichloromethane (DCM), and xylene. Reactive sulfur compounds were not eluted quantitatively with the addition of polar protic solvents such as methanol ($\delta_d$=15.1; $\delta_p$=12.3; and $\delta_h$=22.3). In contrast, it was discovered that the sulfides could be eluted with a solvent mixture including a polar aprotic solvent with a stronger polarizability Hansen solublity parameter ($\delta_d$=15-20; $\delta_p$>7; and $\delta_h$>6). Acetonitrile ($\delta_d$=15.3; $\delta_p$=18.0; and $\delta_h$=6.1) has been especially effective. Apparently, as part of a solvent mixture acetonitrile successfully competes for $Ag^+$ as a ligand complexing agent. By mass action, a large volume of acetonitrile relative to the small quantities of S ligand bonded to $Ag^+$ releases the reactive S compounds. Thus, Ag-SCX can be used to generate two S-rich fractions suitable for further analysis.

Figure 2:
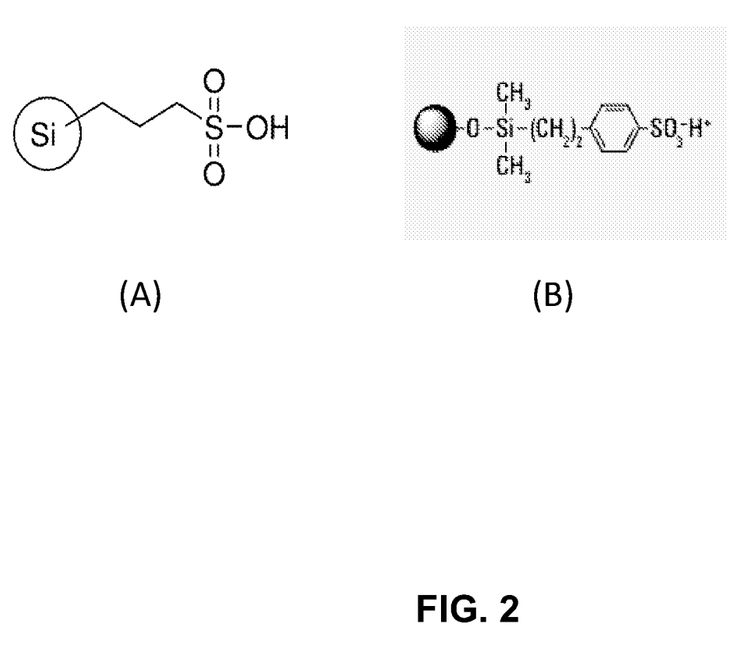
FIG. 2 are exemplary silica based aliphatic and aromatic sulfonic acids.

Several variations of silver impregnated strong cation silica gels have been successfully applied for the separation of reactive (i.e. "corrosive") and unreactive sulfur compounds in petroleum streams. Silica gels derivatized with propyl sulfonic acid functionality (A) or propyl-benzenesulfonic acid (B) have been found suitable as polymeric based aromatic sulfonic acids substrates (FIG. 2). Similar separation could be achieved by using Ag forms of alternate cation ion exchange substrates.

Ion exchange substrates are readily available as cartridges from commercial sources that also supply bulk 3-propylsulfonic acid-functionalized silica gel (Aldrich, Silicycle, J. T. Baker). The method described herein can be carried out with columns packed with this type of substrate. However, both alkyl and aromatic sulfonic acid silicas are available from a variety of sources in the form of pre-packed solid phase extraction (SPE) cartridges and high performance liquid chromatography (HPLC) columns. While examples provided herein use SPE cartridges, it is understood that the invention will apply equally to its application with in house columns packed with bulk substrates, SPE, and HPLC SCX columns. In principle, polymer based substrate analogues (e.g., polystyrene-sulfonic acid) can also be used.

Using SCX silica as an example of suitable cation substrates, a cartridges is pre-wet with an appropriate solvent. This is followed by passage of a diluted solution of silver nitrate in the same solvent through the pre-wet bed of SCX silica thereby converting the SCX from its as supplied to its $Ag^+$ form. A three-fold molar excess of $Ag^+$ is used to ensure counter-ion substitution. After excess $Ag^+$ ions are rinsed from the column with additional aliquots of the same solvent, that solvent is replaced with a non-complexing solvent. Suitable solvents for Ag(I) impregnation are water, methanol, and acetonitrile. Suitable non-complexing solvents as described above include toluene, methylene chloride, and hexane. Prepared cartridges rinsed with 10% acetone in DCM or toluene alone (and wrapped with aluminum foil have been successfully stored in a refrigerator for up to a month).

Example

The 1 g propyl sulfonic acid silica SPE cartridge (Bond Elute PRS, Agilent part #12256010) was chosen for use. A three-fold molar excess for this 0.18 meq/g capacity was calculated to be 90 mg silver nitrate. Therefore, it was prepared for use as follows: The cartridge was pre-wet with 5 ml acetonitrile; converted to Ag(I) form with 3 ml of a 30 mg/ml silver nitrate solution; rinsed with 6 ml acetonitrile then 6 ml 10% acetone in DCM (if that solvent is to be used for the first fraction).

Prior to separation of a sample, the total concentration of sulfur is determined by any number of conventional analytical methods, for example, x-ray fluorescence (XRF). This concentration is used to determine the optimum sample size for separation based on the milliequivalents of silver on the SCX substrate. For separation, the sample is dissolved in a non-complexing solvent mixture with moderate polarity (as described by its solubility parameters in preceding sections). An aliquot containing the appropriate weight of sample is added to the head of a Ag-SCX bed in the cartridge. After the sample has passed into the bed, it is eluted first with an appropriate volume of a moderately polar solvent (as defined above) to elute non-reactive sulfur compounds into one vial. After the first solvent has passed thru the bed such that the liquid level just reaches the top of the bed, a second vial is placed under the cartridge. Then an appropriate volume of the second solvent mixture (complexing solvent as defined above) is used to elute "reactive sulfur" compounds into the second vial. Depending on type of reactive S to be determined (total or sulfides only) the contents of the first vial or both vials are ready for S analysis.

Example

One gram PRS SPE cartridges converted to Ag(I) form as described above have capacity to complex ~2.5 mg sulfur. To ensure that the column is not overloaded the sample aliquot are chosen to keep total S below that value. For a sample with known S content, an appropriate aliquot of toluene solution equivalent was loaded onto the bed in the cartridge. A cartridge was then eluted with an appropriate volume of DCM:acetone (9:1) under gravity flow into the first vial. Then a second vial was positioned under the cartridge and an appropriate volume of DCM:acetonitrile (1:1) was collected in a second vial. The S content in each of isolated fractions was measured by inductively coupled plasma mass spectrometry (ICP-MS). The results are summarized in Table 1.

TABLE 1

Sulfur Separation

| | Sample | | |
|---|---|---|---|
| | A | B | C |
| % S (XRF) | 2.56 | 5.77 | 3.51 |
| mg loaded | 91.3 | 40.7 | 53.8 |
| mg S loaded | 2.33 | 2.35 | 1.89 |
| mg non-corrosive S | 1.66 | 1.01 | 0.86 |
| mg corrosive S | 0.64 | 0.74 | 0.69 |
| S recovery | 2.3 | 1.75 | 1.55 |
| % Recovery | 98.7 | 74.5 | 82.0 |
| % Non-reactive (XRF − ICP) | 71 | 43 | 46 |
| % Non-reactive (ICP + ICP) | 72 | 58 | 55 |

To evaluate the mass and sulfur recovery, a sample of high boiling petroleum fraction with a very low content of thiols was separated with the method above. The weight of sample used for separation was 75 mg. Gravimetric results for two fractions obtained after solvent evaporation gave 60.2 mg in the first fraction and 14.2 mg in the second fraction providing the quantitative mass recovery at 99.2%.

S-measurement for the separated fractions showed that 71.1% of total sulfur (reactive and non-reactive) is distributed in the first fraction and 27.6% is in the second one thus demonstrates 98.7% for sulfur recovery.

Figure 3:
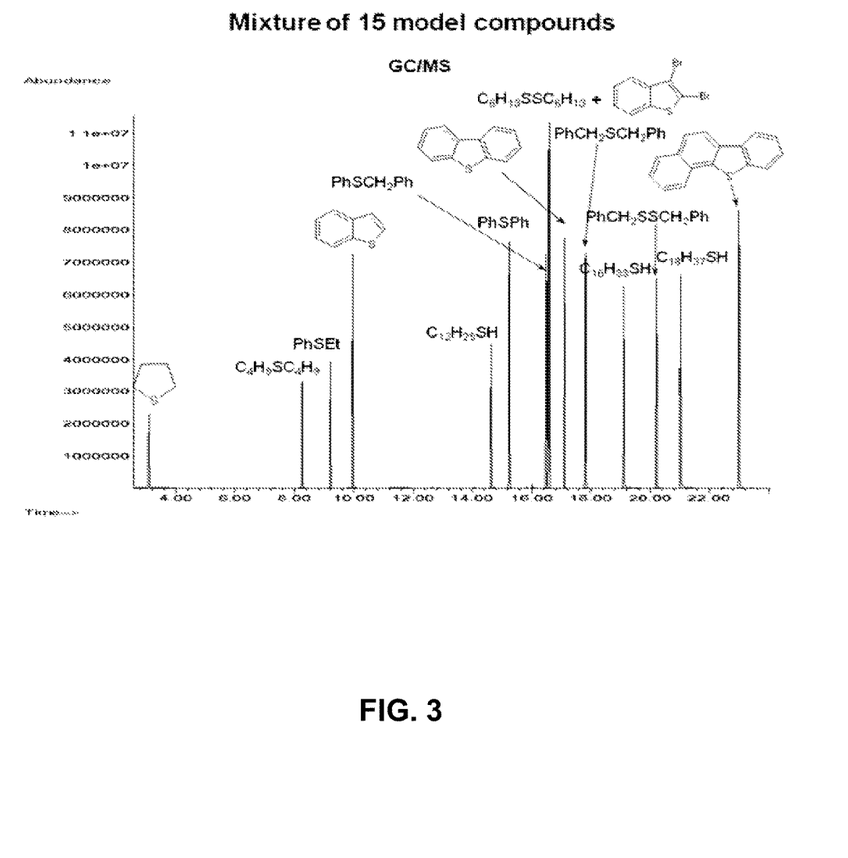
FIG. 3 is a GC/MS for a model compound mix.

The separation of S-classes was validated by GC/MS analysis of a 15 compound model compound mixture (Table 2) before and after separation. Each of the model compounds was resolved and detected with GC/MS (FIG. 3). As can be seen in the subsequent figures, the non-reactive model compounds were eluted in the first fraction (FIG. 4) and the reactives in the second fraction (FIG. 5) where reactive sulfur is eluted with a complexing solvent.

TABLE 2

15 model compounds.

| No | Name, CAS# | Type |
|---|---|---|
| 1 | Tetrahydrothiophene, CAS# 110-01-0 | Reactive |
| 2 | Dibutyl sulfide, CAS# 544-40-1 | Reactive |
| 3 | Ethyl phenyl sulfide, CAS# 622-38-8 | Reactive |
| 4 | Dibenzyl sulfide, CAS# 538-74-9 | Reactive |
| 5 | Benzyl phenyl sulfide, CAS# 831-91-4 | Reactive |
| 6 | 1-Dodecanethiol, CAS# 112-55-0 | Reactive |
| 7 | 1-Hexadecanethiol, CAS# 2917-26-2 | Reactive |
| 8 | 1-Octadecanethiol, CAS# 2885-00-9 | Reactive |
| 9 | Dihexyl disulfide, CAS# 10496-15-8 | Reactive |
| 10 | Dibenzyl disulfide, CAS# 150-60-7 | Reactive |
| 11 | Diphenyl sulfide, CAS# 139-66-2 | Non-reactive |
| 12 | 1-Benzothiophene, CAS# 95-15-8 | Non-reactive |
| 13 | 2,3-Dibromobenzo[b]thiophene, CAS# 6287-82-7 | Non-reactive |
| 14 | Dibenzothiophene, CAS# 132-65-0 | Non-reactive |
| 15 | 1,2-Benzodiphenylene sulfide, CAS# 239-35-0 | Non-reactive |

Figure 4:
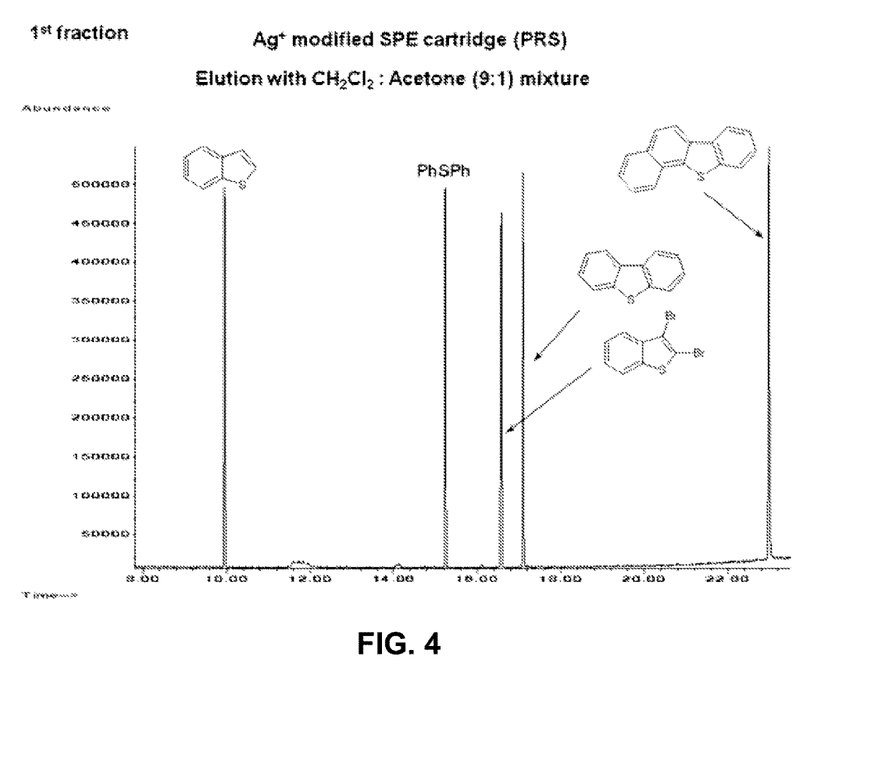
FIG. 4 is a first fraction showing thiophenic (non-reactive) sulfur from Ag-SCX separation.
Figure 5:
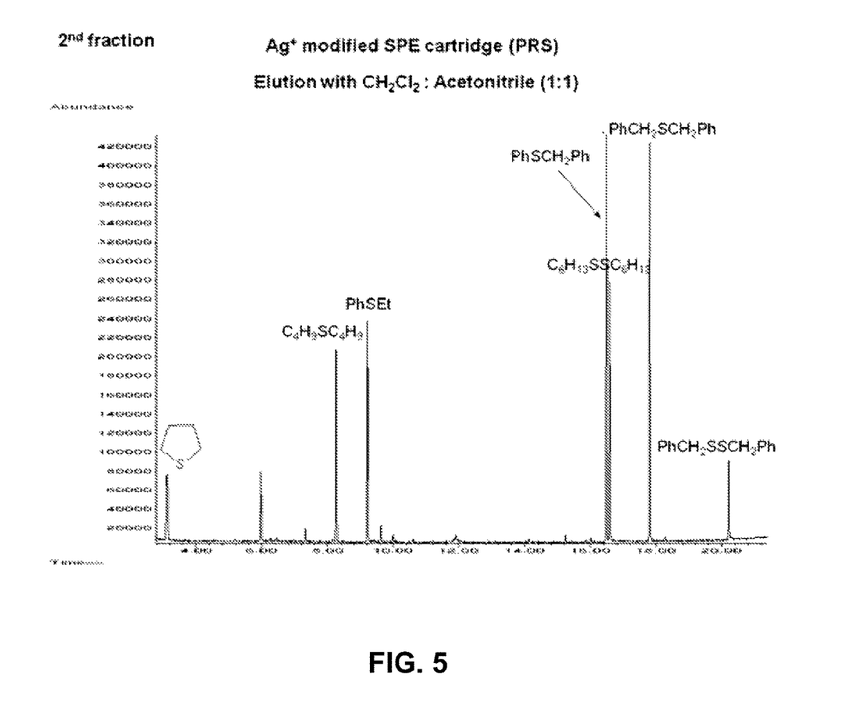
FIG. 5 is a second fraction showing reactive sulfur eluted with complexing solvent.

Despite the large differences in aromaticity (number of aromatic rings) all the thiophenic compounds in the model mix are eluted in the first fraction. Also the dodecyl-, hexadecyl- and octadecyl-mercaptans are not eluted in either fraction. They are retained on the column as thiolates.

Figure 6:
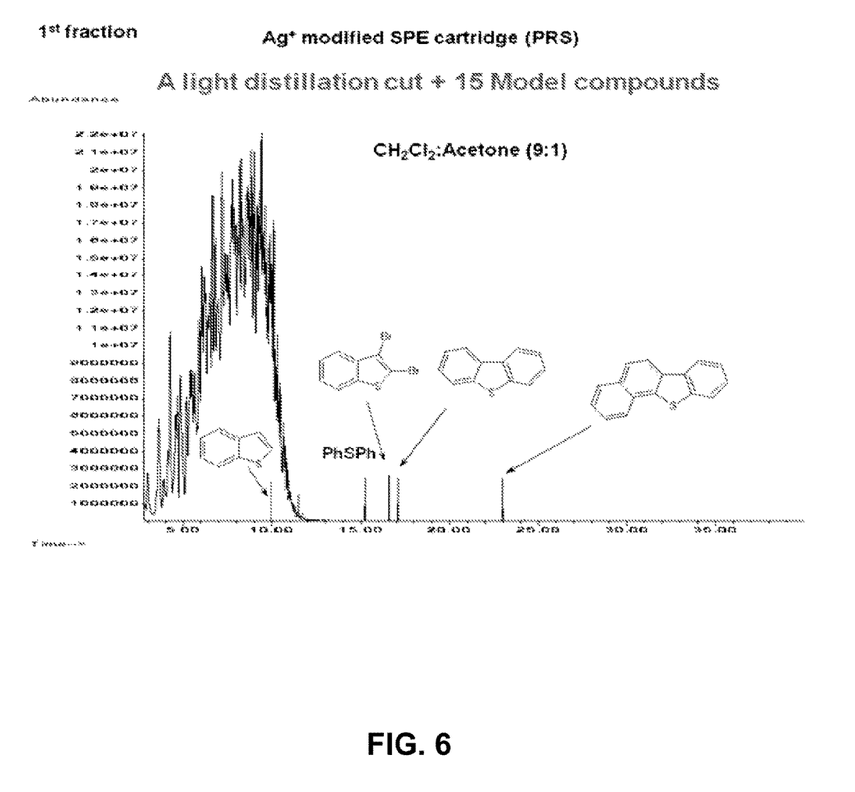
FIG. 6 is a first fraction from a light distillate spiked with the 15 model compound standard.
Figure 7:
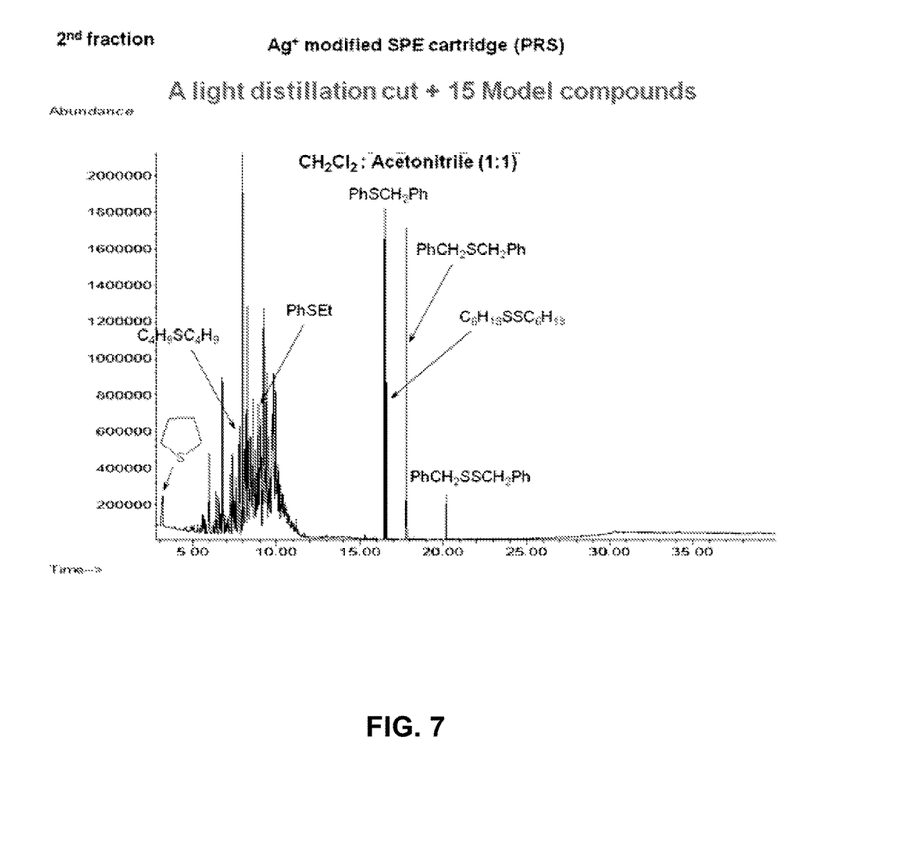
FIG. 7 is a second fraction from light distillate spiked with the 15 model compound standard.

A comparison of the GC/MS for two fractions from a light distillate spiked with the 15 compound standard clearly shows differences in classes of compounds. The first fraction light distillate is shown in FIG. 6 and the second fraction is shown in FIG. 7.

Figure 8:
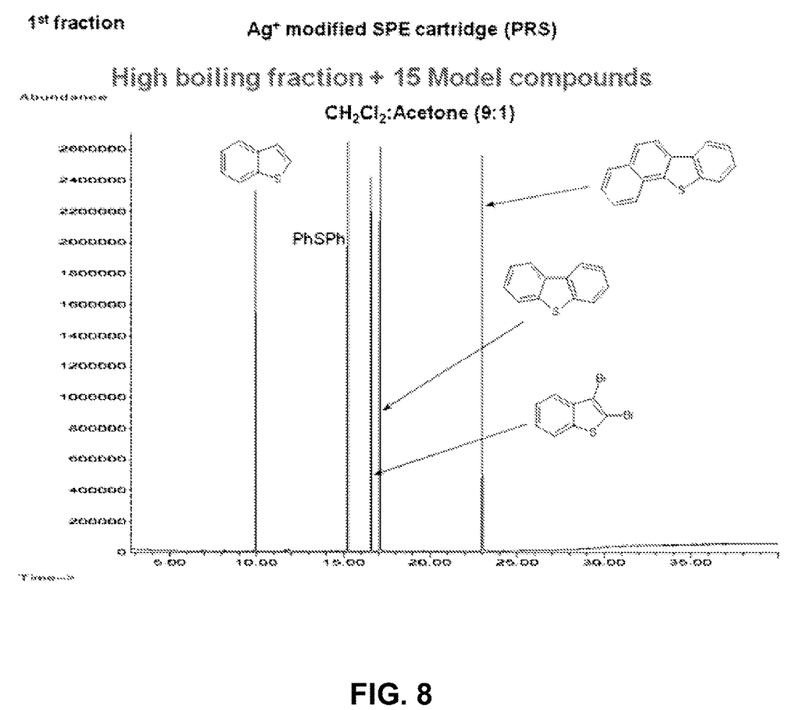
FIG. 8 is a first fraction of the high boiling petroleum sample spiked with the 15 model compounds.
Figure 9:
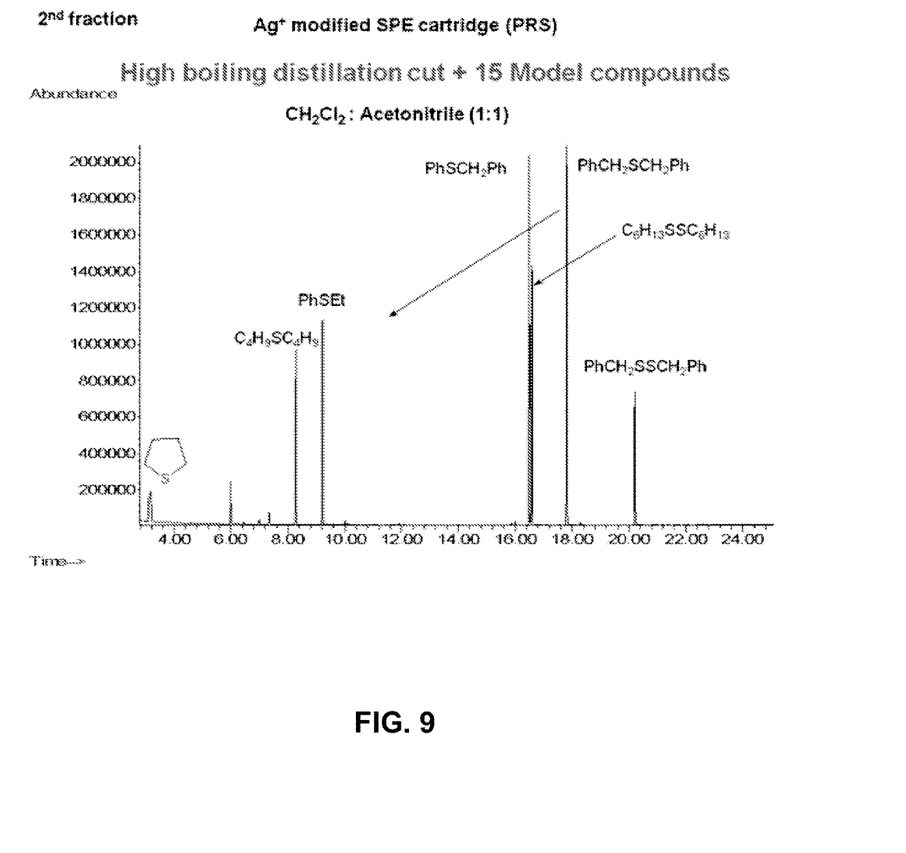
FIG. 9 is a second fraction of the high boiling petroleum sample spiked with 15 model compounds.

The sample plus a 15 model compound spike to the high boiling fraction was dissolved in DCM and subjected to the separation. In this case, none of the components of the heavy oil boil in the range separated and detected under the GC conditions used. As a result, only the model compounds were detected in the first fraction (FIG. 8) and the second fraction (FIG. 9). However, separated fractions by their appearance (dark brown liquids) demonstrate the presence of high-boiling petroleum compounds. Thus, the high-boiling petroleum species do not affect the ability of the method to separate the sulfur types (reactive and non-reactive).

To determine the distribution of "non-reactive" vs. "reactive" sulfur in a petroleum (or petroleum derived) sample one may either A) perform separation with subsequently measure sulfur both fractions, or B) isolate only the first ("non-reactive") fraction and measure its sulfur and calculate the "reactive" sulfur by the difference (total sulfur in the petroleum sample before separation "minus" the first fraction).

Thus, two methods for determination of sulfur content can be envisioned on the basis of this separation:

Method A:

The content of "non-reactive" vs. "reactive" sulfur by measurement of both fractions (contributions from mercaptans that are retained on the column are quantified by difference, i.e. the initial sulfur minus the sum of the two fractions is designated to be mercaptans).

A sample is separated by Ag-SCX into a first ("non-reactive") and the second ("reactive" sulfur minus mercaptans) fractions, and the concentration of S determined for each. Mercaptans (that are not isolated in either fraction) may be determined independently by standard methods to account for their contribution to "reactive S".

Method B:

The content of "non-reactive" vs. "reactive" sulfur by difference (includes mercaptans, sulfides, and disulfides as "reactive S").

Figure 10:
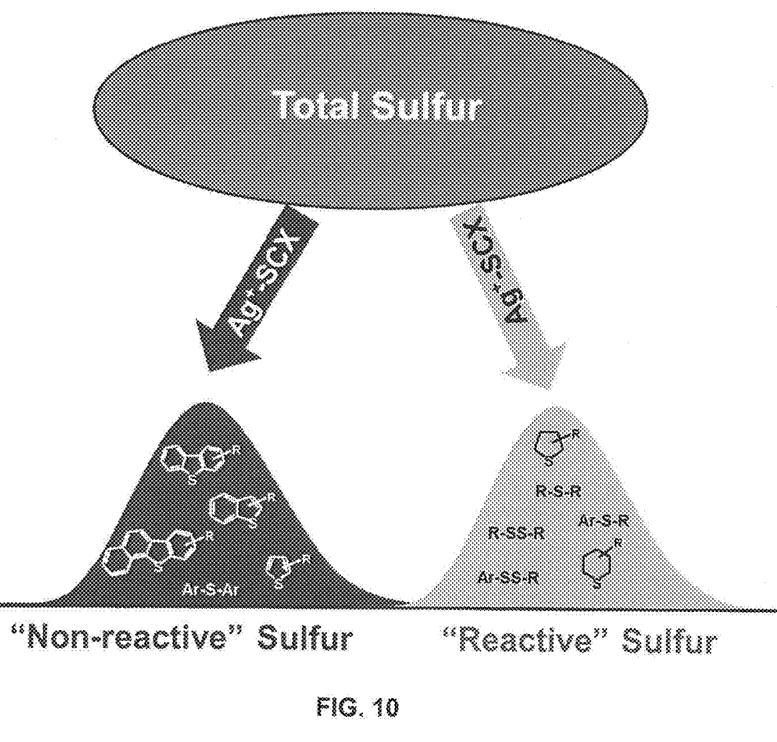
FIG. 10 is a schematic diagram illustrating the separation of reactive and non-reactive sulfur from total sulfur content.

An un-separated sample and its "non-reactive" fraction isolated by Ag-SCX method are analyzed for sulfur and the "reactive sulfur" is calculated by difference. The separation is only carried out to isolate the "non-reactive" fraction. Mercaptans (that are not isolated in either fraction and retained on the column) are included in the "reactive S" by calculation. If desired, the contribution of mercaptans and disulfides to the "reactive" sulfur can be determined by existing standard methods. By difference the contribution of sulfides may be estimated. FIG. 10 is a schematic diagram illustrating the separation of reactive and non-reactive sulfur from total sulfur content.

Various aspects of the invention can be presented in a range format. It should be understood that the description in the range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range for example, 1, 2, 2.7, 3, 4, 5, 5.3 and 6. This applies regardless of the bread of the range. The disclosures of all references cited herein are hereby fully incorporated by reference.

This invention can be embodied in other forms without departing from the spirit or essential attributes thereof, and accordingly, reference should be had to the following claims to determine the scope of the invention.

We claim:

1. A method to determine the content of sulfur in the form of non-reactive sulfur compounds and reactive sulfur compounds in whole petroleum samples by separating non-reactive sulfur compounds from reactive sulfur compounds in a petroleum composition, comprising the steps of:

contacting the whole petroleum composition with a Ag-containing silica cation exchange media in an exchange column, the silica comprising surface hydroxyl groups and wherein Ag+ is ionically bonded to the surface hydroxyl groups;

contacting the petroleum composition and the Ag-containing cation exchange media with a non-reactive sulfur compound solvent capable of eluting the non-reactive sulfur compounds in the presence of the Ag-containing cation exchange media and incapable of eluting the reactive sulfur compounds in the presence of the Ag-containing cation exchange media at the conditions of the exchange, wherein:

the non-reactive sulfur compounds comprise at least one selected from the group consisting of:

Thiophene the non-reactive sulfur compound solvent has Hansen solubility parameters of $\delta_d=17\text{-}20$; $\delta_p=0\text{-}7.0$; and $\delta_h<7$;

eluting from the exchange column, without backflushing, the non-reactive sulfur compounds from the media with the non-reactive sulfur compound solvent to provide a first fraction;

determining the amount of non-reactive sulfur compounds in the first fraction;

contacting the petroleum composition and the Ag-containing cation exchange media with a reactive sulfur compound solvent, the reactive sulfur compound solvent being a stronger silver complexing agent than the non-reactive sulfur compound solvent, and being capable of eluting the reactive sulfur compounds to provide a second fraction, wherein:

the reactive sulfur compounds comprise at least one selected from the group consisting of:
$R_1SH$—Thiol (mercaptans)
$R_1SR_2$—Sulfides (including cyclic)
$R_1SSR_2$—Disulfides
where $R_1$, $R_2$ can be H, alkyl, cycloalky or aryl groups connecting to S-atom directly or through alkyl groups, and $R_1$, $R_2$ can further comprise heteroatoms (O,N,S), and diaryl sulfides are non-reactive sulfur compounds;

the reactive sulfur compound solvent having Hansen solubility parameters of $\delta_d=15\text{-}20$; $\delta_p>7$; and $\delta_h>6$;

eluting from the same exchange column, without backflushing, the reactive sulfur compounds from the media with the reactive sulfur compound solvent to provide a second fraction;

and, determining the amount of reactive sulfur compounds in the second fraction.

2. The method of claim 1, wherein the stationary phase media comprises at least one selected from the group consisting of silica, polymer, or nano-dispersed media.

3. The method of claim 1, wherein the reactive sulfur compounds comprise at least one selected from the group consisting of mercaptans, disulfides, and sulfides.

4. The method of claim 1, wherein the non-reactive sulfur compounds comprise thiophenic sulfur compounds and diaryl sulfides.

5. The method of claim 1, wherein the non-reactive sulfur compound solvent is at least one selected from the group consisting of toluene, dichloromethane, and acetone.

6. The method of claim 1, further comprising the step of measuring the sulfur content of the eluted non-reactive sulfur compounds.

7. The method of claim 6, further comprising the step of, after eluting the reactive sulfur compounds with a reactive sulfur compound solvent, measuring the sulfur content of the eluted reactive sulfur compounds.

8. The method of claim 7, further comprising the step of calculating of the sulfur content from mercaptans in the reactive sulfur compounds.

9. The method of claim 6, further comprising the step of determining the total sulfur content of the petroleum sample, and determining the sulfur content of the reactive sulfur compounds and the sulfur content of the non-reactive sulfur compounds.

10. The method of claim 1, further comprising the step of diluting the petroleum composition with an organic solvent prior to contacting the petroleum composition with the Ag-containing cation exchange media.

11. The method of claim 1, wherein the non-reactive sulfur compound solvent is a supercritical fluid at the conditions of the exchange.

* * * * *